(12) United States Patent
Fadem (10) Patent No.: US 9,259,164 B2
(45) Date of Patent: Feb. 16, 2016

(54) CONTROLLER FOR NEUROMUSCULAR TESTING

(75) Inventor: Kalford C. Fadem, Louisville, KY (US)

(73) Assignee: Neuronetrix, Inc., Louisville, KY (US)

( * ) Notice: Subject to any disclaimer, the term of this patent is extended or adjusted under 35 U.S.C. 154(b) by 1086 days.

(21) Appl. No.: 12/064,057

(22) PCT Filed: Aug. 21, 2006

(86) PCT No.: PCT/US2006/032675
§ 371 (c)(1),
(2), (4) Date: Aug. 15, 2008

(87) PCT Pub. No.: WO2007/022524
PCT Pub. Date: Feb. 22, 2007

(65) Prior Publication Data
US 2008/0312551 A1    Dec. 18, 2008

Related U.S. Application Data

(60) Provisional application No. 60/709,966, filed on Aug. 19, 2005.

(51) Int. Cl.
*A61B 5/05* (2006.01)
*A61B 5/04* (2006.01)
*A61B 5/00* (2006.01)
*A61B 5/11* (2006.01)

(52) U.S. Cl.
CPC ........... *A61B 5/04001* (2013.01); *A61B 5/4041* (2013.01); *A61B 5/4047* (2013.01); *A61B 5/1106* (2013.01)

(58) Field of Classification Search
CPC ............. A61B 5/04001; A61B 5/4029; A61B 5/4035; A61B 5/4041; A61B 5/4047; A61B 5/4076; A61B 5/459
USPC ...................................................... 600/554
See application file for complete search history.

(56) References Cited

U.S. PATENT DOCUMENTS

| 5,381,805 A | 1/1995 | Tuckett et al. |
| 5,540,235 A | 7/1996 | Wilson |
| 5,551,446 A | 9/1996 | Chutkow et al. |

(Continued)

FOREIGN PATENT DOCUMENTS

| WO | WO 92/19156 | 11/1992 |
| WO | WO 2004/112604 | 12/2004 |

OTHER PUBLICATIONS

ESR dated Feb. 28, 2008 for International Application No. PCT/US2006/032675.

(Continued)

*Primary Examiner* — Lee S Cohen
*Assistant Examiner* — Emily Lloyd
(74) *Attorney, Agent, or Firm* — Frost Brown Todd LLC (57) ABSTRACT

A peripheral nervous system (PNS) neuromuscular disorder testing system incorporates a testing apparatus that is affixed to a patients skin, positioning a stimulus transducer (e.g., electrical contact(s), movable sharp point, etc.) into a nerve pathway of interest with an electrode and reference electrodes appropriately positioned relative thereto to measure the electrical signal produced. A wireless connection to a control box relays the data associated with the time of the stimulus and the sensed response to a diagnostic system that analyzes the waveform per selectable testing protocols with user tailorable view capabilities and data dissemination communication paths.

14 Claims, 7 Drawing Sheets

(56) References Cited

U.S. PATENT DOCUMENTS 5,730,146 A 3/1998 Itil et al.
7,179,231 B2 * 2/2007 Ezenwa .................. 600/554

OTHER PUBLICATIONS

International Preliminary Report on Patentability dated Feb. 20, 2008 for Application No. PCT/US2006/032675.

* cited by examiner

| Stimulus Settings ||
|---|---|
| Stimulus Type | Tactile, electrical, vibratory |
| Duration | How long the stimulus will last |
| Delay | How long between each stimulus |
| Sequence | The order in which stimuli are presented |
| Amplitude | The strength of the stimulus |
| Waveform | The shape of the stimulus profile |

FIG. 7

| Data Capture Settings ||
|---|---|
| Electrode Location | Location on the body of each electrode |
| Electrode Selection | Which electrodes will be selected for data capture |
| Data Capture Start-End | When should the data capture begin and end |
| Data Capture Rate | What rate should the system sample the electrodes to capture data |
| Signal Gain | Signal amplification |
| Artifact Threshold | Voltage threshold to be used to instruct the system when to replay the stimulus set |

FIG. 8

CONTROLLER FOR NEUROMUSCULAR TESTING

CROSS REFERENCE TO RELATED APPLICATIONS

The present application is a national entry of PCT International Patent Application Ser. No. PCT/US06/032675, entitled "CONTROLLER FOR NEUROMUSCULAR TESTING," filed 21 Aug. 2006, published as WO/2007/022524 on 22 Feb. 2007; which claims the benefit of U.S. Pat. Appln. Ser. No. 60/709,966, "CONTROLLER FOR NEUROMUSCULAR TESTING", filed 19 Aug. 2005, the disclosure of which is hereby incorporated by reference in its entirety.

Subject matter in the present application is related to subject matter disclosed in co-pending and commonly-owned PCT International Patent Application Ser. No. PCT/US2005/021272, entitled "EVOKED RESPONSE TESTING SYSTEM FOR NEUROLOGICAL DISORDERS", filed 16 Jun. 2005, published as WO/2006/009771 on 26 Jan. 2006; which in turn claimed the benefit of U.S. Pat. Appln. Ser. No. 60/580,853, "AUDITORY EVOKED RESPONSE MAPPING SYSTEM FOR AUDITORY NEUROME", filed 18 Jun. 2004, the disclosures of both of which are hereby incorporated by reference in their entirety.

Subject matter in the present application is related to subject matter disclosed in co-pending and commonly-owned U.S. patent application Ser. No. 11/154,192 entitled "DEVICE AND METHOD FOR TRANSMITTING PHYSIOLOGIC DATA", filed 16 Jun. 2005, published as U.S. Pub. No. 2005/0280531 on 22 Dec. 2005; and PCT International Pat. Appln. PCT/US05/21257 entitled "WIRELESS ELECTRODE FOR BIOPOTENTIAL MEASUREMENT", filed 16 Jun. 2005, published as WO/2006/009767 on 26 Jan. 2006; both claiming the benefit of U.S. Pat. Appln. Ser. No. 60/580,776 entitled "DEVICE AND METHOD FOR TRANSMITTING PHYSIOLOGIC DATA" and U.S. Pat. Appln. Ser. No. 60/580,772 entitled "WIRELESS ELECTRODE FOR BIOPOTENTIAL MEASUREMENT", both filed 18 Jun. 2004, the disclosures of all of which are hereby incorporated by reference in their entirety.

The present application is related to co-pending and commonly-owned PCT International Patent Application Publ. No. WO 2006/026548, "BIOPOTENTIAL WAVEFORM DATA FUSION ANALYSIS AND CLASSIFICATION METHOD", published 9 Mar. 2006, which claimed the benefit of the U.S. provisional patent application entitled "EVOKED RESPONSE POTENTIAL DATA FUSION ANALYSIS METHOD", Ser. No. 60/605,630, filed on 30 Aug. 2004, the disclosures of which are hereby incorporated by reference in their entirety.

FIELD OF THE INVENTION

The present invention relates generally to a method and apparatus for peripheral nervous system (PNS) nerve conduction tests for neuromuscular disorders such as carpal tunnel syndrome, cubital tunnel syndrome, non-localizing back pain, diabetic neuropathy, and other peripheral, polyneuropathic, and/or neuromuscular conditions. by capturing brain waves produced while processing a preprogrammed peripheral stimulus.

BACKGROUND OF THE INVENTION

The clinical features of impaired nerve function arise from disturbances in the structure of the cell body (neuronopathy), its axon (axonopathy), or the myelin coverings of the axon (myelinopathy). Disturbed function of peripheral nerves (neuropathy) can occur when chronic ischemia (associated with vascular disease) or inflammation prevents delivery of critical levels of nutrients and oxygen to the affected nerve fibers. Neuropathies can involve one (mononoeuropathy) or more nerves (polyneuropathy). Neuropathy can affect primarily sensory or motor fibers or may affect both types of fibers (sensorimotor neuropathy).

Reversible symptoms of disrupted nerve conduction occur with localized acute ischemia due to compression of the vascular supply to the affected nerves such as occurs with sitting in one position for an extended period of time. Such conditions are associated with weakness, numbness and paraesthesias or "pins and needles" in the affected limb, which are early clinical signs of peripheral neuropathy. These symptoms are readily relieved with change in position and the restoring of blood flow to the affected area. Similar reversible disturbances of sensory nerve conduction occur with local anesthetics (e.g., cocaine) and with exposure to certain chemicals (e.g., pyrethrins) that impede nerve conduction by disrupting sodium transport across neuronal cell membranes. Small unmyelinated nerve fibers are more susceptible to the effects of local anesthetics and thus these chemicals are ideal for producing anesthesia without paralysis. Metabolic disturbances such as levels of increased blood glucose and metabolites associated with diabetes can also produce a sensorimotor neuropathy.

The neuronopathies are characterized by pathological changes that begin in the cell body. Pyridoxine neurotoxicity is an example of a sensory neturonopathy and is characterized by chromatolysis (dissolution of Nissl substance and margination of the nucleus to the periphery of the cell body) followed by disintegration of the cell body and axon (i.e., necrosis) and its myelin sheath. Regeneration does not occur in the neuronopathies because the cell body is destroyed. Amyotrophic lateral sclerosis, or Lou Gehrig's Disease, (anterior horn cell disease) and polio are examples of motor neuronopathies. In neuronopathy and axonopathy (below) secondary muscle atrophy occurs.

A peripheral nerve fiber that is crushed or compressed undergoes Wallerian degeneration, which is characterized by disintegration of segments of the axons and myelin sheaths distal to the site of injury. The Schwann cells surrounding the severed portion of an axon stop synthesizing new myelin and the existing myelin breaks down to form myelin ovoids. The injured cell soon generates new axons front growth-cones that form at the end of the old axon above the site of injury. The surviving Schwann cells divide and remyelinate the new axon as it grows within the original basal lamina.

Complete transection of the axon and its surrounding connective tissues significantly hampers functional recovery as the axon does not have a preserved basal lamina to direct its growth back toward its original site of innervation. Aberrant collateral sprouting occurs and may be associated with additional functional disturbances due to the development of abnormal patterns of sensorimotor innervation.

Distal central-peripheral axonopathy is a process similar to Wallerian degeneration, in that the axonal continuity is interrupted and secondary demyelination occurs. This can occur as a result of "chemical transection" of the axon with the subsequent disintegration of the axon and myelin sheath distal to the site of the lesion. This pathological process is often preceded by paranodal swellings with associated accumulations of neurofilaments, which are visible on microscopic examination. Longer axons are more vulnerable to the effects of a neurotoxicant induced chemical transection and thus, nerve fibers of the lower extremities are typically affected first. Regeneration occurs with cessation of exposure to the offending neurotoxicant and begins with the proliferation of Schwann cells and the formation of growth cones from which new axonal processes develop.

Myelinopathies are characterized by disintegration of myclin sheath with preservation of the axon. Myelinopathies may be due to toxic exposures, infections, or immune-mediated inflammatory responses (e.g., Guillain-Barre syndrome). Compression of the nerve also disrupts myelin which in turn impedes conduction of nerve impulses and slows nerve conduction velocities. Cardinal features of myelinopathy include segmental demyelination, wherein the myelin of some internodes is damaged with preservation of others. The breakdown of internodal myelin appears as ovoids along the course of the intact axon. Motor nerves are composed of more heavily myelinated fibers than are sensory nerves and thus motor nerves are more susceptible to the effects of trauma and pressure such as entrapment injury that occurs within the carpal tunnel. Remyelination occurs with removal of the offending agent or condition of entrapment. The myelinated nerve is altered by the presence of internodes of different lengths which can affect the conduction characteristics of the peripheral nerve.

One approach that has been suggested is described in U.S. Pat. Nos. 6,936,012; 6,692,444; 6,507,755; 6,379,313; 6,266,558; 6,146,335; 6,132,387; 6,132,386; 5,976,094; and 5,851,191, whose teachings are apparently incorporated in an NC-stat system available from NeuroMetrix, Inc., of Waltham, Mass., and described at http://www.neurometrix.com/products.htm. The NC-stat system consists of the following four components: (1) A battery-powered monitor—The monitor contains the electronic circuitry and software required to provide initiate and control the nerve conduction study, acquire and save patient and test information including the response waveforms, display information on the LCD readout, and transmit data to the docking station. LCD displays include the distal motor latency (DML) value, the distal sensory latency (DSL) value, the Sensory Nerve Action Potential (SNAP) amplitude value, the F-wave latency value, limb indicator (left or right), low battery indicator, the memory slot being used to store the test data, and user messages (menu selections, sensor serial numbers, device status, operator instructions, and error conditions). (2) A docking station used to download the test data to the onCall Information System via an analog phone line. (3) Single-use, disposable biosensors are available for the median motor, ulnar motor, median motor & sensory, ulnar motor & sensory, posterior tibial, deep peroneal and sural nerves. (4) The onCall Information System for automatic generation of the hardcopy patient test report, which includes test results (DML, Compound Muscle Action Potential—CMAP—amplitude, DSL, SNAP amplitude, conduction velocity, F-wave latency, and associated response waveforms) and a comparison of patient results to normal ranges. Reports are sent to the user by facsimile or e-mail.

An example of application of the generally known NC-stat system is to described in the article "Clinical Utility of the NC-stat System in the Patient with Low Back Pain Point-of-Care Evaluation of Lumbosacral Radiculopathy" by Shai N. Gozani, MD, PhD, excerpted below:

Low back pain is one of the most frequent forms of morbidity in industrialized nations and is the second most common reason for visiting a physician in the United States. While most back pain episodes resolve quickly, a significant number require immediate intervention or develop into chronic conditions. Low back pain, particularly in patients with radiating symptoms or weakness, is often associated with compromise of the lumbosacral nerve roots through mechanical and biochemical means. The diagnostic assessment of the patient with possible radiculopathy may include magnetic resonance imaging (MRI) and electrodiagnostic (EDX) studies. These two modalities are complementary. MRI provides high-resolution visualization of the lumbar soft tissue structures but suffers from high false positive rates. EDX studies have high sensitivity and specificity but may not provide the same degree of localization as MRI. In addition, traditional EDX studies require specialist referral, are expensive, and are uncomfortable for the patient. The NC-stat nerve conduction testing system addresses these to a certain extent issues by providing clinicians with a physiological assessment of the lumbosacral nerve roots and lower extremity nerves, at the point of patient care.

When evaluating patients with low back pain, the NC-stat system is used to assess the distal and proximal neurophysiologic function of the peroneal and tibial nerves. In each test, two types of signals are measured: M-waves and F-waves. Both are myoelectrical potentials evoked by non-invasive electrical stimulation of the appropriate nerve at the ankle. The M-wave is generated by conduction of the neural impulse from the point of stimulation to the innervated muscles and is typically reported as a latency (distal motor latency, DML) and an amplitude. The F-wave response is generated by antidromic ("reverse") neural propagation from the point of stimulation through the nerve roots into motor neurons of the spinal cord, backfiring of the motor neurons, and then orthodromic ("forward") conduction to the innervated muscles. The F-wave is a complex signal that may be characterized by a number of different parameters, although in traditional clinical use only the earliest ("minimum") latency is typically utilized. The NC-stat system incorporates signal processing algorithms that analyze multiple parameters of F-waves.

Neuropathology alters both the M-wave and the F-wave signals. M-wave changes generally indicate disease that is predominately distal, such as entrapment of the nerve at the ankle, or polyneuropathy (e.g. diabetic neuropathy). However, proximal pathology causing axonal loss can also alter M-wave characteristics. The F-wave reflects conduction along the entire length of the nerve and is thus diagnostically sensitive to neuronal injury anywhere from the spinal cord to the inverted muscle, including: nerve root compromise, proximal nerve compression, distal nerve entrapment syndromes, plexopathies, and systemic neuropathies. An overview of the electrodiagnostic interpretation of peroneal and tibial nerve abnormalities as follows:

A normal NC stat Study has an electrodiagnostic interpretation of no electrodiagnostic evidence of nerve root or peripheral nerve pathology. An isolated peroneal Fwave abnormality NC stat Study would have a typical clinical finding of acute or chronic low back/leg pain with an electrodiagnostic interpretation of L5/S1 radiculopathy. An isolated tibial F-wave abnormality NC stat Study would have a typical clinical finding of acute or chronic low back/leg pain based upon an electrodiagnostic interpretation of L5/S1 radiculopathy. A bilateral peroneal and tibial F-wave NC stat Study would have typical clinical findings of chronic low, back and leg pain abnormalities, normal or mild DML abnormalities based upon electrodiagnostic interpretation based on Polyradiculopathy (lumbar stenosis). A bilateral DML and F-wave NC stat Study has a typical clinical finding of foot numbness abnormalities of peroneal and tibial, relative DML changes often greater than F-wave based upon an electrodiagnostic interpretation of Polyneuropathy. A unilateral tibial DML abnormality NC stat Study with a typical clinical finding of foot pain and sensory loss on plantar surface of feet based on electrodiagnostic interpretation of distal tibial neuropathy (tarsal tunnel syndrome). A unilateral peroneal DML abnormality NC stat Study with a typical clinical finding of foot pain and sensory loss in the D1-2 web space based on an electrodiagnostic interpretation of distal peroneal neuropathy. Thus, nerve root involvement is generally indicated by F-wave abnormalities in the presence of normal or mildly altered distal nerve function.

While generally-known systems do provide a clinical tool for diagnosing certain disorders of the peripheral nervous system, these systems have certain limitations in that their diagnostics is confined to certain functionality incorporated into an end-user device. Consequently, a significant need exists for an improved peripheral nervous system (PNS) nerve conduction test apparatus and method for neuromuscular disorders.

BRIEF SUMMARY OF THE INVENTION

The invention overcomes the above-noted and other deficiencies of the prior art by providing peripheral nervous system (PNS) nerve testing systems and methods for testing for neuromuscular disorders which is easy to configure and use; enables standardized protocols and methods; facilitates testing of a broad range of neurological attributes and disorders; and delivers reliable and reproducible results.

In one aspect of the invention, a PNS testing system may be used for peripheral nervous system (PNS) evaluations by generating a sequence of various stimuli through transducer(s) in contact with the skin. The peripheral stimulus is detected by receptors in the skin which produce electric signals in the form of action potentials which are then sent to the central nervous system (CNS). These action potentials produce a time varying voltage potential on the surface of the skin which can be detected with a plurality of skin electrodes.

This system enables a variety of stimuli to be produced with precise control over the intensity, duration, and waveform of each stimulus, along with the sequence of different stimuli and the time delay between each stimulus. This protocol can be configured in the system and downloaded into the control box for presentation to the patient. The measured skin voltages, which reflect the performance of the PNS, can then be uploaded to an online database for visualization or analysis by a pattern recognition engine.

A unique aspect of this system is in the protocol creation functions, downloading the protocols into the control box, maintaining the logic of the stimuli sequences, and analyzing the responses with a fusion classifier, as compared to generally known PNS testing systems that may only view very specific aspects of the response. Additional testing protocols allow one of a number of different stimuli or stimuli with different time delays to record numerous responses and then train the fusion method to more precisely diagnose PNS disorders.

In another aspect of the invention, a PNS testing system has a distributed network architecture that meets the needs for economical testing at clinical locations, yet provides advantages of a standardized large population test data repository at a remote site. Test protocols may be user-defined and then stored on a remote and/or distributed element, such as accessed over the Internet or similar network, for later use. Similarly, test protocol configurations, stimulus files, and results may be stored in a remote and/or distributed database. This may include having all protocols used in any test which results in data being captured to be permanently stored in a centralized database for data integrity, economic processing, and large population analyses and research validation. Typically, all results stored in the centralized database may be related to a particular test protocol, allowing results to be queried by test protocol parameters. All stimulus files used in any testing protocol that results in data being captured may be permanently stored in a centralized database.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
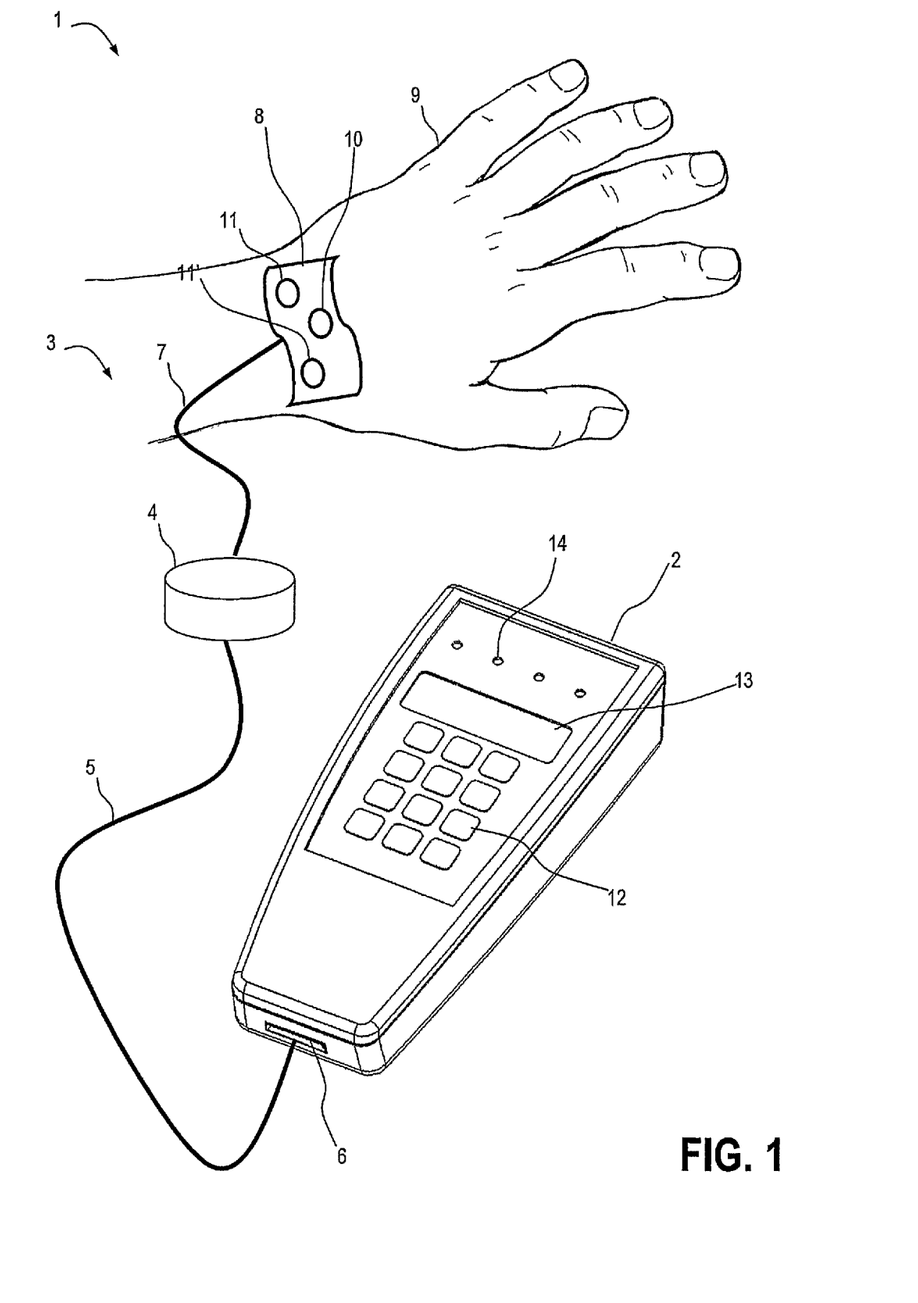
FIG. 1 is a perspective view of a peripheral nervous system (PNS) nerve conduction testing apparatus, positionable at the wrist, used for diagnosing neuromuscular disorders consistent with aspects of the invention.

In the drawings where like members are given the same reference numeral, FIG. 1 depicts a peripheral nervous system (PNS) testing device 1 that provides tactile stimulation and detects the nerve conduction response. A battery powered control unit 2 (described in the cross referenced WO 2006/026548 WO 2006/009771), which allows portability of diagnostic data taking allows use whenever and wherever desired, is connected to a PNS electrode apparatus 3 which is composed of an amplifier module 4 connected to the control unit 2 via cable 5 which is plugged in to port 6. The amplifier module 4 is also connected to an electrode array 8 via cable 7. Electrode array 8 can be adhesively affixed to a peripheral body location 9. Electrode array 8 includes a stimulus generator 10 which provides a means of generating tactile stimuli such as electrical impulses, a projecting sharp point, and/or a vibration to generate a neuromuscular response. Detector contacts 11 and 11' provide a means to detect the electrical neuromuscular response to the tactile stimulus. The Control unit 2 includes a button panel 12 with which a user may enter alphanumeric information, a visual display 13 with which system or testing information may be displayed, and illumination devices 14 to display system status.

Economy of use is achieved by centralized processing of the diagnostic data so that a great number of PNS testing devices 1 may be used without the necessity of expensive waveform processing equipment at each location. Collecting data from many tested individuals enables enhanced and improved diagnostic algorithms to be created and implemented. Furthermore, the PNS testing device 1 includes features that speed its use while avoiding human error and the need for extensive training.

Figure 2:
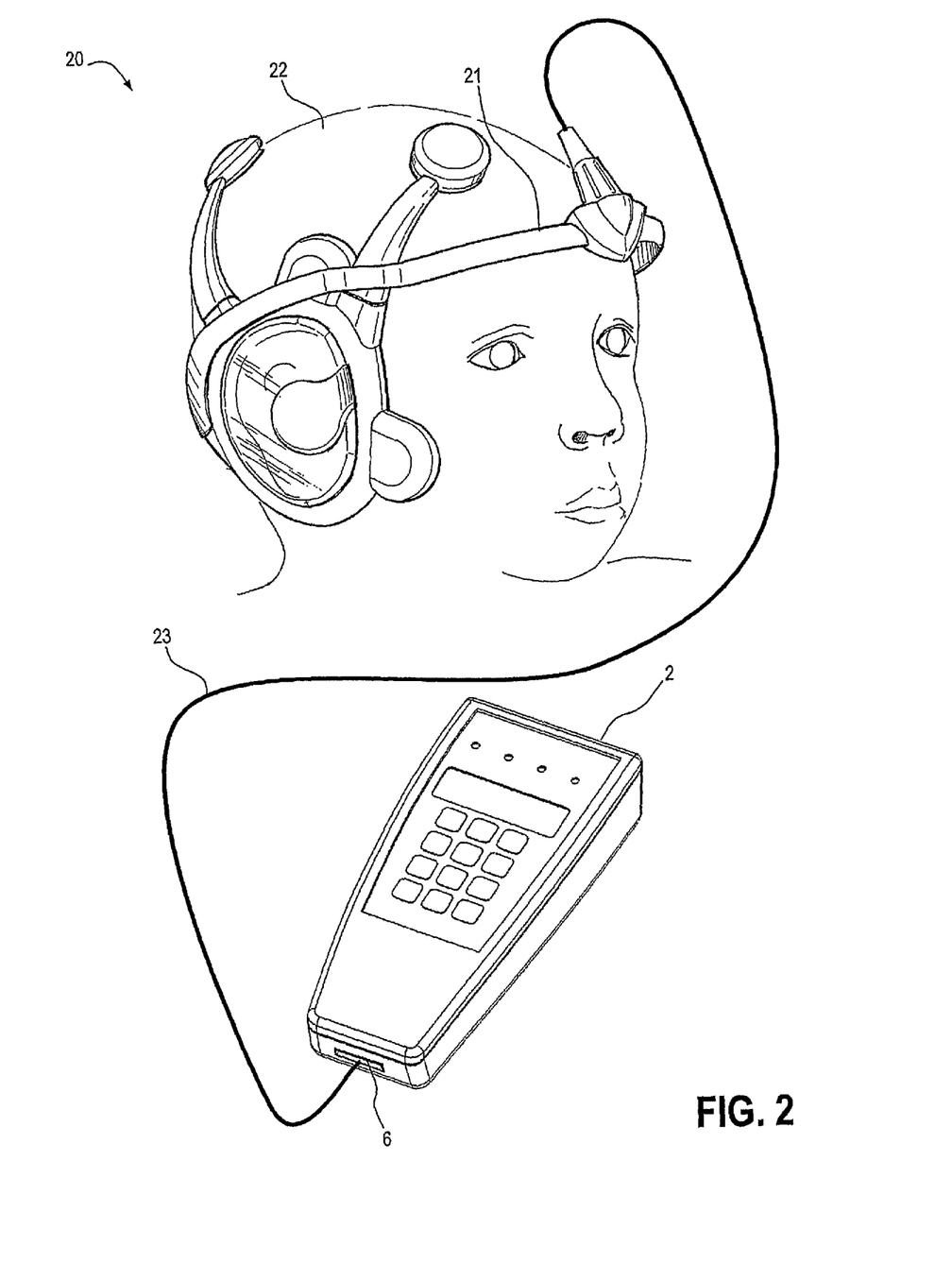
FIG. 2 is a perspective view of and evoked response potential testing apparatus used for diagnosing neurological disorders consistent with aspects of the invention.

FIG. 2 depicts an alternative screening system, whereby the control unit 2 may be connected to an evoked response potential headset 21 via cable 23 which is plugged into port 6. The evoked response potential headset 21 which produces an auditory or visual stimulus is placed on the head of a subject 22 for the purpose of performing evoked response potential tests.

Figure 3:
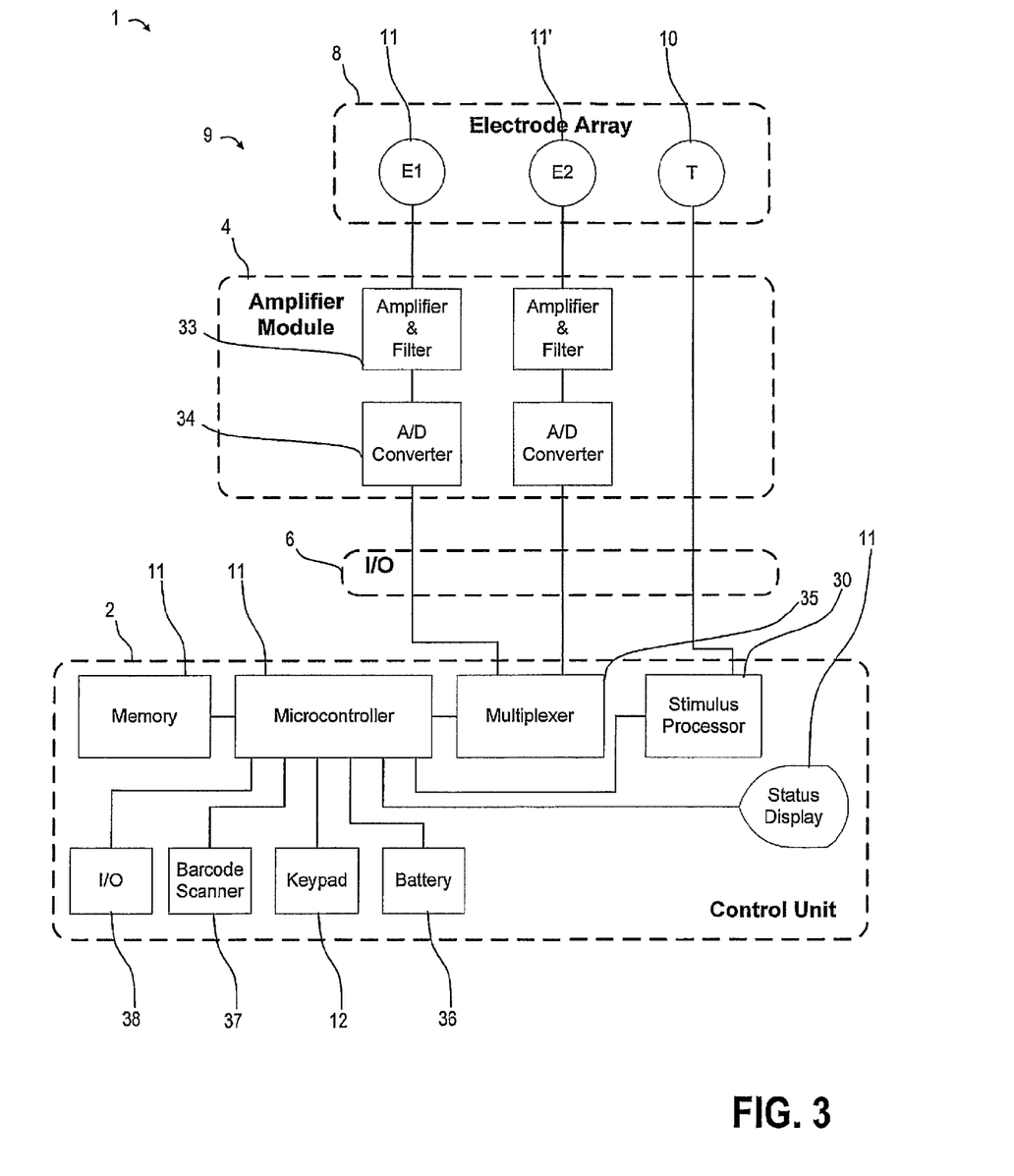
FIG. 3 is a functional block diagram of a peripheral nervous system (PNS) nerve conduction testing apparatus.

FIG. 3 depicts an electrical block diagram of the PNS test system. In response to a tactile stimulus generated by stimulus generator 10 incorporated within electrode array 8 which has been affixed to a peripheral body location 9, detector contacts 11 and 11' detect the minute skin voltage potentials produced by the body's neuromuscular system. The tactile stimulus is generated via a stimulus processor 30 within the control unit 2. The duration, delay, sequence, amplitude, waveform, and other attributes of the tactile stimulus are controlled by microcontroller 31 with instructions stored in memory 32. The skin voltage potentials from contact detectors 11 and 11' are amplified and filtered with circuit 33 and converted to digital form with A/D converter 34. The data is multiplexed with multiplexer 35 and stored in memory 32. The PNS testing system 1 is powered by a rechargeable battery 36. User input can be entered with keypad 12. Patient identification information may be input using an onboard barcode scanner 37. Communication with a computer communication network can be accomplished with communication I/O 38 which can be either wired or wireless.

In an alternative embodiment, amplifier module 4 may be integrated within the control unit 2 by including amplifier and filter circuits 33 and A/D converter 34 within control unit 2.

Figure 4:
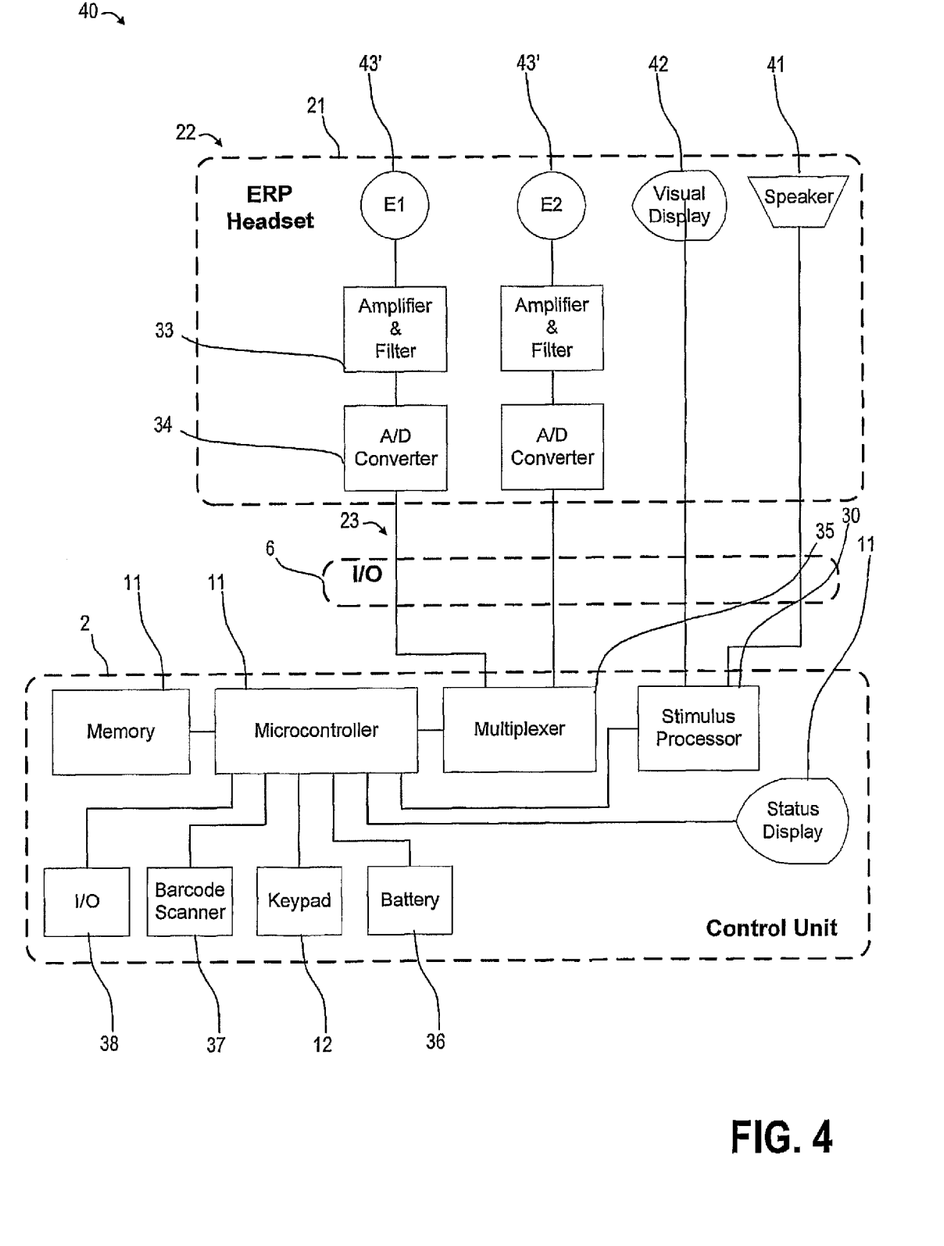
FIG. 4 is a block diagram of a network to support nerve conduction testing consistent with aspects of the invention.

FIG. 4 depicts an electrical block diagram of an ERP test system 40 which uses control unit 2 to control the administration of the ERP test and to record the test data. In this embodiment ER-P headset 21 is affixed to subject's head 22 and connected to control unit 2 via cable 23 which plugs into port 6. An auditory stimulus is produced via stimulus processor 30 which is sent to speaker 41 which to produce an auditory evoked response. Alternatively, a visual stimulus is produced by stimulus processor 30 and sent to visual display 42 to produce a visual evoked response. Evoked response electrical skin potentials are picked up by electrodes 43 and 43'. The signals are amplified and filtered with circuit 33 and converted to digital form with A/D converter 34. The data is multiplexed with multiplexer 35 and stored in memory 32. The ERP testing system 40 is powered by a rechargeable battery 36. User input can be entered with keypad 12. Patient identification information may be input using an onboard barcode scanner 37. Communication with a computer communication network can be accomplished with communication I/O 38 which can be either wired or wireless.

In an alternative embodiment, amplifier and filter circuits 33 and A/D converter 34 may be integrated within the control unit 2.

Figure 5:
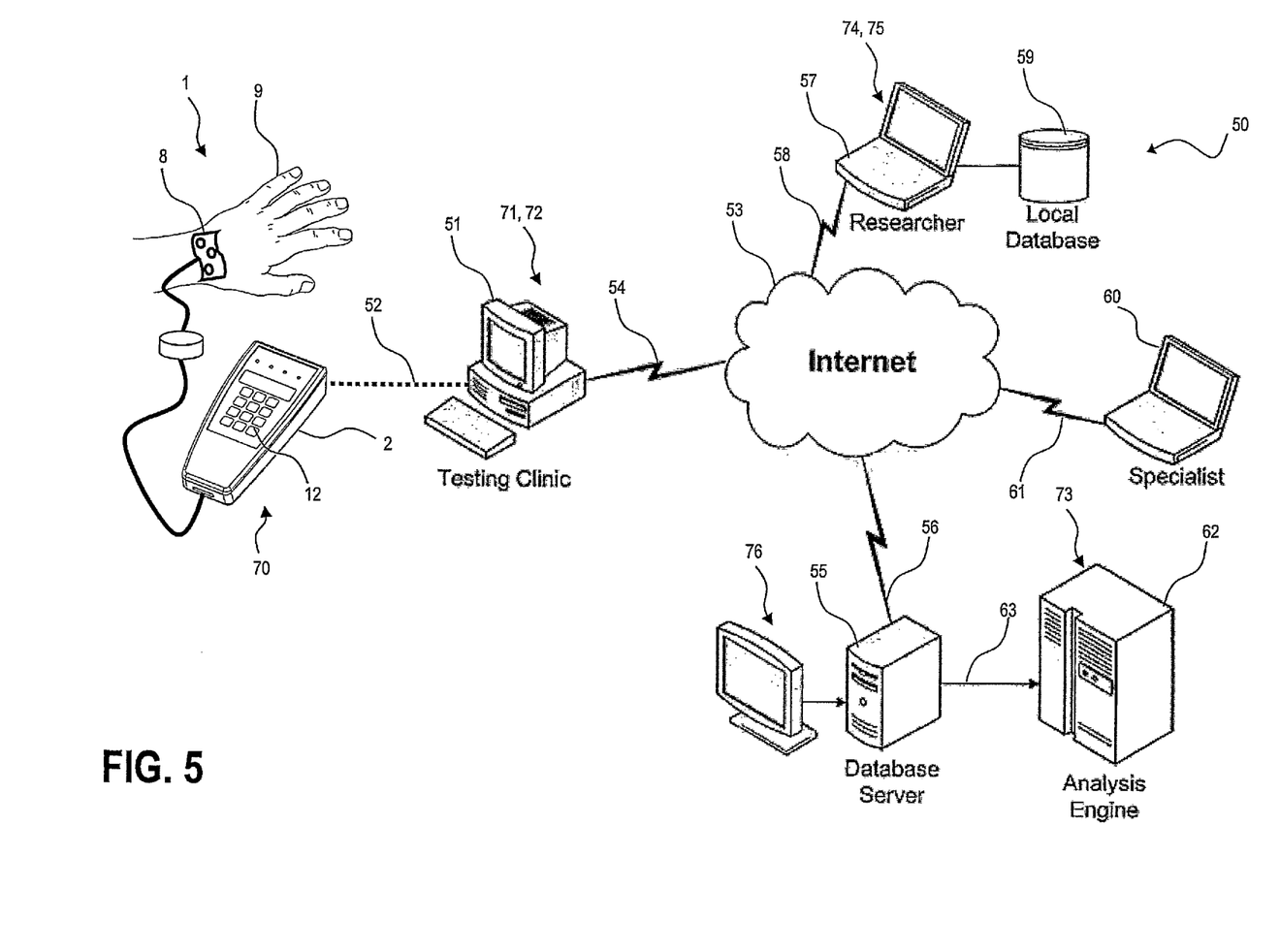
FIG. 5 is a functional block diagram of a nerve conduction testing protocol consistent with aspects of the invention.

FIG. 5 depicts a PNS testing system that advantageously provides for economical testing, billing, long-term data storage and analysis for analysis refinement, subsequent therapeutic measures, and other features. To this end, the control unit 2 of PNS testing device 1 may be in electrical communication with a hospital system 51 via a cable or wireless link 52 so that accomplishment of the PNS test, may be performed under the control of headset firmware 70. The PNS testing system 50 also facilitates use of electrode array 8 attached to a peripheral location 9 that responds to protocol provided in the firmware 70 to perform a desired PNS nerve conduction test that is analyzed by backend data processing components of the system 62.

In particular, administration of the test is controlled through a control panel software application 71, which provides testing protocols for tactile stimulus, duration, delay, sequence, amplitude, waveform, and other attributes. Additional information is noted for patient health records and for billing records through an electronic medical records (EMR) software application 72. Also, the hospital system 51 may facilitate communication across a network, such as the Internet 53 via a wired or wireless connection 54 to a remote processing facility, depicted as database server 55 which may also be connected to the Internet 53 via a wired or wireless connection 56. Analysis using a classifier software application 73 may be performed remotely on a researcher computer 57 connected wired or wirelessly 58 to the Internet 52 or on an analysis computer 62. Users of the PNS testing device 1 may access the system 50 through researcher computer 57 for the purpose of creating testing protocols with the protocol editor software application 74 or visualizing testing results using viewer software application 75. Users may access the PNS testing system 50 for the purpose of evaluating patient tests through physician (specialist) computer 60 connected to the Internet 53 through wired or wireless connection 61. Users may also store data on a database 59 connected to their own computers 57 and 60. Administrators of the system 50 may have direct access to the system database on database server 55 through management console software application 75.

The database server computer 55 and analysis computer 62 allow for the most up-to-date analysis methods to be employed to diagnose a PNS disorder. Moreover, historical data may be mined as recognition techniques improve to capture previously undiagnosed conditions or to otherwise correlate previous test results with other forms of data to further refine the diagnostic process. It should be appreciated that the analysis performed by the analysis computer 62 could further include neural network processing, wherein the neural network is trained to recognize a waveform characteristic of various PNS disorders.

Positive, inconclusive, and/or negative screening test results may be forwarded to an appropriate recipient, such as a specialist 60 for further diagnostic testing and/or therapeutic measures.

Figure 6:
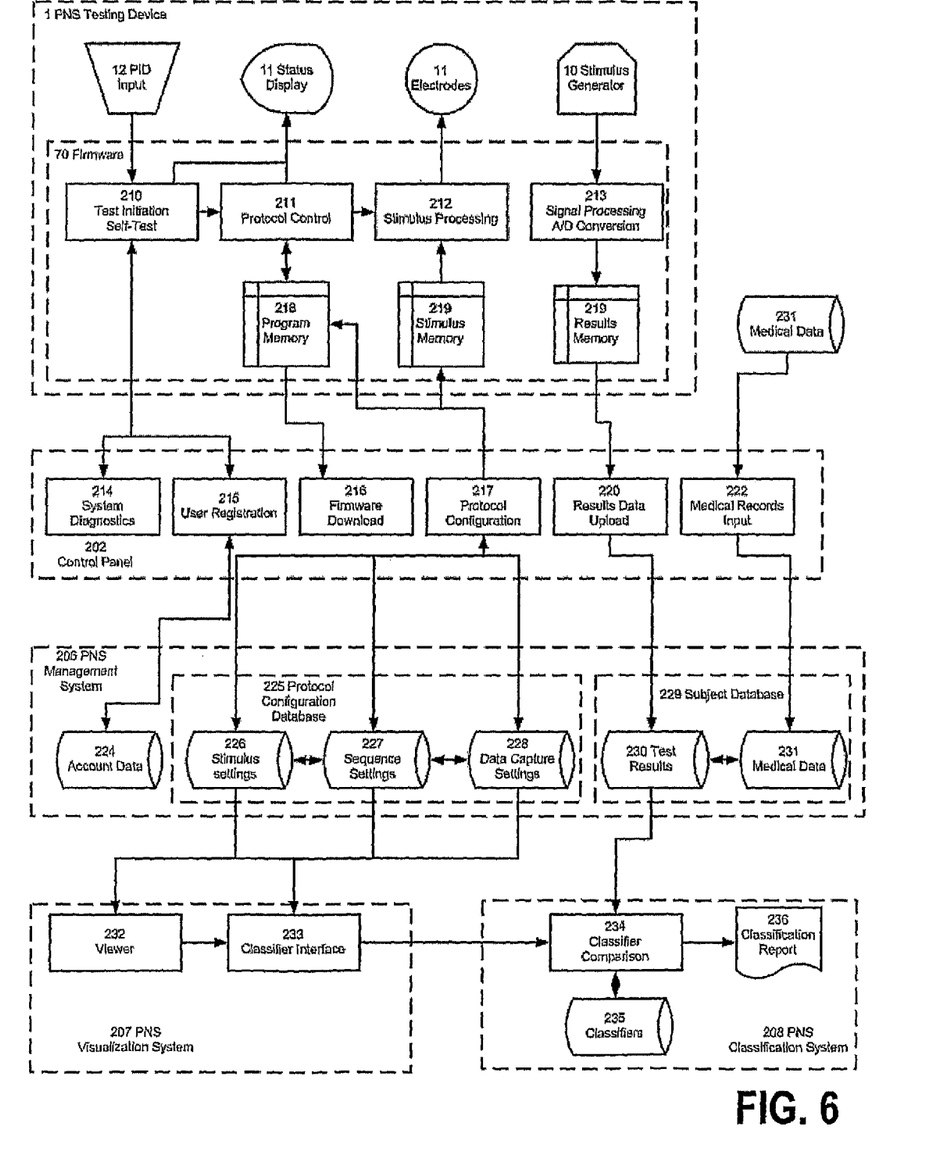
FIG. 6 is a functional block diagram of the control system and information flow of a peripheral nervous system (PNS) nerve conduction testing system.

FIG. 6 depicts a system to program a PNS device, perform a PNS test, upload the test data, view the test data, and perform an analysis and classification. The PNS test device (block 1) contains input/output devices including a patient identification means (block 12), a stimulus generator (block 10), and electrodes (block 11). The PNS test device (block 1) is controlled through on-board firmware (block 201) which performs functions such as test initiation and self-test (block 210), protocol control (block 211), stimulus preprocessing (block 212), and signal processing and A/D conversion (block 213). The PNS test device (block 1) is programmed through a web-enabled control panel application (block 202). The control panel (block 202) communicates with the PNS firmware (block 201) to perform a system diagnostic (block 214), register the PNS device (block 1) and any users (block 215), to download the latest firmware (block 216), to configure the desired test protocol (block 217) and load those protocols and stimulus data into the PNS device memory (block 218 and block 219 respectively), upload test results (block 220) from the test result memory (block 221), and input medical record information (block 222) from a hospital medical record database (block 223). The control panel (block 202) also communicates with the management system (block 206) which contains an account database (block 224), a protocol configuration database (block 225), and a subject database (block 229). The protocol configuration database (block 225) stores protocol information such as stimulus settings (block 226), stimulus sequence settings (block 227), and the data capture settings (block 228). The subject database (block 229) stores all PNS test results (block 230) and any medical data (block 231) about the subject being tested. Testing results (block 230) may be viewed on a computer using the PNS visualization system (block 207) which includes two modules for viewing the PNS waves (block 232) and for inputting various settings (block 233) for the PNS classifier application (block 234). The PNS classifier (block 234) compares subject test results (block 230) resulting from a specific testing protocol (block 225) against a database of known classification templates (block 235) and then generates a classification report (block 236).

It should be appreciated that specific neuromuscular disorders may be accurately diagnosed by using a fusion classifier application described in the aforementioned published PCT application WO 2006/026548. The recorded biopotential signals may be uploaded to the test results database (block 230) and may be visualized with the viewer application (block 232). Classifiers for various neuromuscular disorders could be generated with the classifier application (block 233), then stored in the classifier database 235. A system as described above would benefit from the ability to easily and remotely create, store, download, and utilize new and custom test protocols. Protocols could include time varying stimuli and multiple testing configurations. The online database would allow the creation of improved classifiers and our fusion classifier application would provide more accurate diagnoses.

Figure 7:
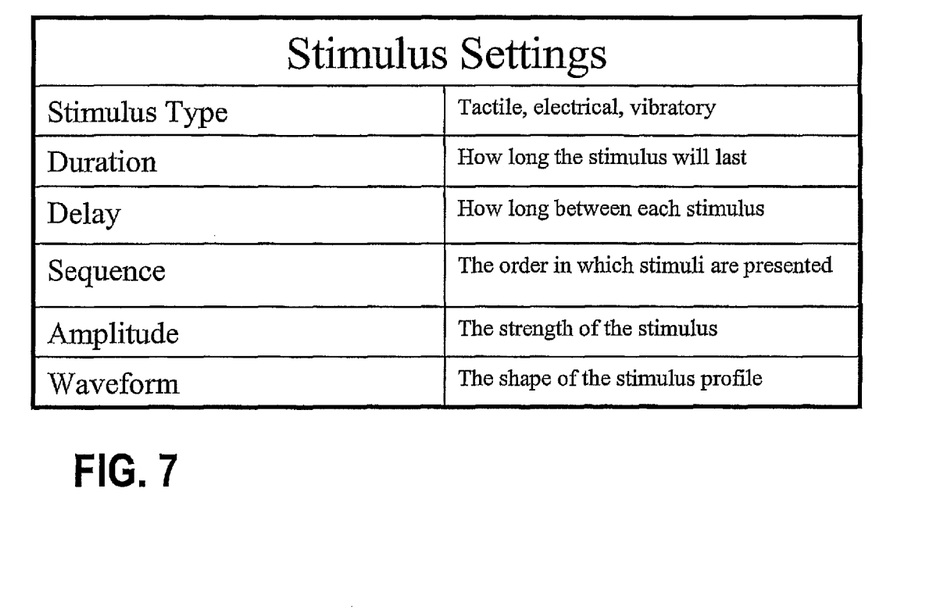
FIG. 7 is a table of PNS stimulus parameters.

In FIG. 7, an illustrative stimulus library is depicted having seven general types of stimulus, representing the kind of tactile stimuli that can be downloaded into control unit memory to be used to evoke a PNS response. Any recorded, or synthesized stimulus parameters may be used with this list being merely exemplary.

Figure 8:
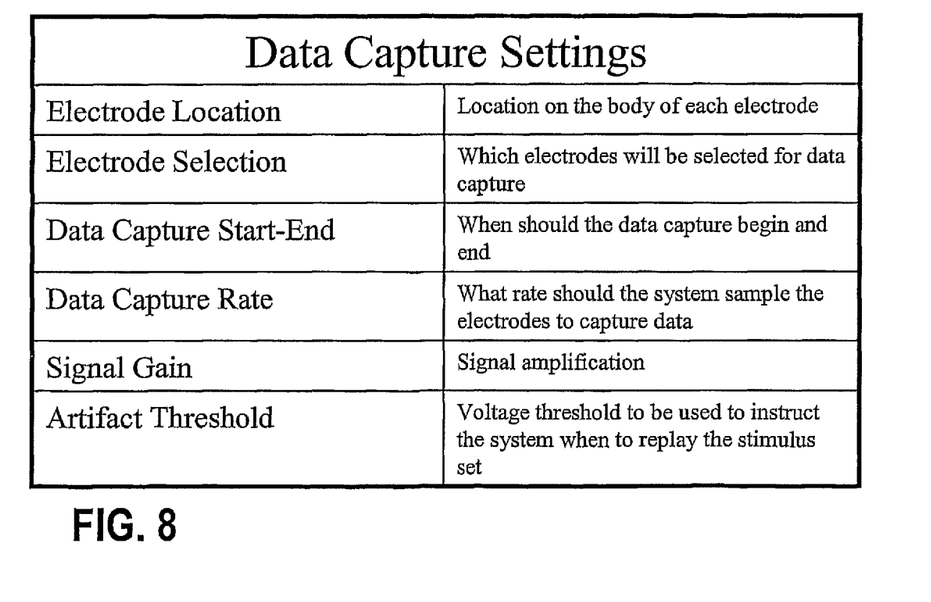
FIG. 8 is a table of PNS data capture settings.

In FIG. 8 an illustrative table is depicted which lists data capture settings that may be accessed, selected, modified, or otherwise utilized by the PNS device 1 to adapt its testing capabilities. For instance, a range of preset electrode locations may be configurable. Data capture start and end defines what latency is expected for the PNS wave of interest. Data capture rate sets what rate the system should sample the electrodes to capture data. Signal gain sets amplification as appropriate for the particular electrode location. In addition, artifact detection parameters may be advantageously incorporated so as to determine if a particular PNS test did not receive an undisturbed result. This artifact detection may be a voltage threshold that should not be exceeded during the data sampling.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A kit operable to perform both evoked response potential (ERP) and peripheral nervous system (PNS) testing, the kit comprising:
   a PNS testing device positionable upon a subject's skin having a signal electrode, a reference electrode and a tactile stimulus producer;
   an ERP testing device configured to perform an ERP test;
   a control unit device operably configured to communicate a plurality of testing control administration parameters to the testing devices, wherein the control unit device is operable to perform both a peripheral nervous system nerve conduction test with the PNS testing device and an evoked response potential test with the ERP testing device, wherein the control unit device comprises a first port that is selectively connectable to a selected one of the PNS testing device or the ERP testing device;
   a remote storage device, wherein the remote storage device is configured to store classifiers associated with a plurality of neuromuscular disorders;
   a computer processor device in communication with the remote storage device, wherein the computer processor device is remote from the control unit device, wherein the computer processor device is configured to receive PNS test results and ERP test results from the control unit device, wherein the computer processor device is configured to compare the PNS test results or ERP test results from the control unit device against the classifiers stored on the remote storage device to correlate the PNS test results or ERP test results with one or more of the neuromuscular disorders, wherein the computer processor device is further configured to generate additional classifiers based at least in part on the PNS test results or ERP test results, the additional classifiers being associated with one or more neuromuscular disorders; and
   a second port in communication with the control unit device, wherein the the a second port is configured to:
   (i) provide remote registration of the control unit device with the computer processor device via a communication network,
   (ii) provide communication of one or more PNS testing protocols or ERP testing protocols from the computer processor device to the control unit device via the communication network, and
   (iii) provide communication of the PNS test results or ERP test results from the control unit device to the computer processor device via the communication network,
   wherein the testing control administration parameters communicated from the control unit device to the testing devices are provided in accordance with the one or more PNS testing protocols or ERP testing protocols.

2. The kit of claim 1, wherein the tactile stimulus producer comprises an electrically actuated projecting member to jab the skin.

3. The kit of claim 1, wherein the tactile stimulus producer comprises a pair of selectively electrified contacts.

4. The kit of claim 1, wherein the plurality of testing control administration parameters are selected from a group consisting of a stimuli start time, a stimuli selection, a stimuli sequence, a failure determination, and sample mode.

5. The kit of claim 1, wherein the computer processor device is further configured to perform PNS diagnostic analyses on the PNS test results.

6. The kit of claim 1, wherein the control unit device further comprises:
- a memory;
- a paradigm logic library, wherein the memory is configured to store paradigm logic information in the paradigm logic library;
- a stimulus library database, wherein the memory is further configured to store stimulus information in the stimulus library database;
- a program contained in the memory; and
- a controller operatively configured to access the memory to perform the program, the program operably configured to access a selected testing paradigm contained in the paradigm logic library, to access stimuli specified by the selected testing paradigm contained in the stimulus library database, to calculate sequence and interstimulus delays between selected stimuli in accordance with the selected testing paradigm, and to output a testing stream associated with the testing paradigm.

7. The kit of claim 6, wherein the controller is further operatively configured to receive PNS test results, wherein the controller is further operatively configured to store the PNS test results in association with subject identification information and the selected testing paradigm.

8. The kit of claim 1, wherein the testing device is further operatively configured to detect an artifact contained in sensed test results, to access an epoch grouping of stimuli associated with the artifact, and to replay the associated epoch grouping.

9. The kit of claim 1, wherein each of the testing devices includes a unique registration code associated with sensed testing results acquired by each of the testing devices.

10. The kit of claim 1, wherein the testing device further comprises a user input feature that is responsive to a manual input from the subject performed in response to a stimulus, the control unit device being operatively configured to receive and store the PNS test results or ERP test results in association with the manual inputs.

11. The kit of claim 1, further comprising a computer system and a graphical user interface operatively configured to access testing results associated with subject identification information and selected testing paradigms, to generate a display of a template of a stored data manipulation parameters, and to generate a display of automatic paradigm-specific grouping.

12. The kit of claim 1, further comprising a computer system and graphical user interface operatively configured to access PNS testing results associated with subject identification information and selected testing paradigms, to access a selected digital signal processing parameter, to access a selected PNS grouping criteria, to access an algebraic combination configuration, to calculate an algebraic combination of the PNS testing results, and to pattern match the combined PNS test results against a neurological PNS model.

13. The kit of claim 12, wherein the computer system is further configured to correlate subsequent neurological diagnoses associated with subject identification information and refine a selected neurological PNS model to correlate with PNS test results associated with the neurological diagnoses.

14. The kit of claim 1, wherein the testing device is positionable at the subject's wrist.

* * * * *